United States Patent
Omlor et al.

(10) Patent No.: US 11,803,045 B2
(45) Date of Patent: Oct. 31, 2023

(54) 3D CALIBRATION BODY, CALIBRATION METHOD FOR THE SPATIAL CALIBRATION OF AN OPTICAL IMAGING SYSTEM, CALIBRATION ELEMENT AND CALIBRATION METHOD FOR CALIBRATING AN OPTICAL IMAGING SYSTEM

(71) Applicant: Carl Zeiss Meditec AG, Jena (DE)

(72) Inventors: Lars Omlor, Pleasanton, CA (US); Carsten Glasenapp, Oberkochen (DE)

(73) Assignee: Carl Zeiss Meditec AG, Jena (DE)

( * ) Notice: Subject to any disclaimer, the term of this patent is extended or adjusted under 35 U.S.C. 154(b) by 853 days.

(21) Appl. No.: 16/458,039

(22) Filed: Jun. 29, 2019

(65) Prior Publication Data
US 2020/0004003 A1     Jan. 2, 2020

(30) Foreign Application Priority Data

Jun. 29, 2018    (DE) ............... 10 2018 115 824.6

(51) Int. Cl.
*G02B 21/00* (2006.01)
*G02B 21/06* (2006.01)
(Continued)

(52) U.S. Cl.
CPC ........ *G02B 21/025* (2013.01); *A61B 5/0077* (2013.01); *A61B 90/39* (2016.02);
(Continued)

(58) Field of Classification Search
CPC . G02B 5/00; G02B 5/003; G02B 5/20; G02B 5/201; G02B 5/204; G02B 5/205;
(Continued)

(56) References Cited

U.S. PATENT DOCUMENTS 5,442,674 A    8/1995   Picard et al.
8,032,321 B2 *   10/2011   Zhong ............. G01N 33/48771
                                         702/19
(Continued)

FOREIGN PATENT DOCUMENTS

| DE | 10051370 A1 | 5/2002 |
| WO | 2015169345 A1 | 11/2015 |
| WO | 2016209654 A1 | 12/2016 |

OTHER PUBLICATIONS

Office Action issued in German Patent Application No. DE 10 2018 115 824.6, dated Jun. 6, 2019 (from which this application claims priority) and English language translation thereof.
(Continued)

*Primary Examiner* — Thong Q Nguyen
(74) *Attorney, Agent, or Firm* — Ewers IP Law PLLC; Falk Ewers (57) ABSTRACT

A 3D calibration body for spatial calibration of an optical imaging system includes a transparent body and calibration marks embedded in a volume of the transparent body. At least some of the calibration marks are selectively activatable and deactivatable, wherein an activated calibration mark is visible in the visible spectral range and a deactivated calibration mark is not visible in the visible spectral range.

13 Claims, 5 Drawing Sheets

(51) Int. Cl.
  *G02B 21/02*  (2006.01)
  *G02B 21/22*  (2006.01)
  *A61B 5/00*  (2006.01)
  *A61B 90/00*  (2016.01)
  *G01M 11/02*  (2006.01)

(52) U.S. Cl.
  CPC ......... *G02B 21/0012* (2013.01); *G02B 21/22* (2013.01); *A61B 2090/3937* (2016.02); *G01M 11/02* (2013.01)

(58) Field of Classification Search
  CPC ... G02B 5/22; G02B 5/23; G02B 5/24; G02B 5/28; G02B 5/282; G02B 5/285; G02B 5/3016; G02B 5/3041; G02B 5/3058; G02B 21/00; G02B 21/0012; G02B 21/0016; G02B 21/0032; G02B 21/0064; G02B 21/0096
  USPC ................ 359/237–325, 577–590, 885–895, 359/368–398
  See application file for complete search history.

(56) References Cited

U.S. PATENT DOCUMENTS

| | | |
|---|---|---|
| 2002/0085668 A1 | 7/2002 | Blumhofer et al. |
| 2004/0004762 A1 | 1/2004 | Bruehl et al. |
| 2015/0103401 A1* | 4/2015 | Park .................. G02B 21/34 359/396 |
| 2015/0150435 A1 | 6/2015 | Morrissette et al. |
| 2016/0129283 A1 | 5/2016 | Meir et al. |
| 2017/0074649 A1 | 3/2017 | Engel et al. |
| 2017/0289534 A1 | 10/2017 | Grundhöfer et al. |

OTHER PUBLICATIONS

Bernhard E.H. Claus, "Geometry Calibration Phantom Design for 3D Imaging", Proc. SPIE 6142, Medical Imaging 2006: Physics of Medical Imaging, 61422E, Mar. 2, 2006.

* cited by examiner

FIG. 5 deactivated calibration mark is not visible in the visible spectral range. A calibration mark is considered not to be visible if the Michelson contrast of the calibration mark in the transparent medium is less than 0.2, in particular less than 0.1. Advantageously, the calibration marks can be activated and deactivated in different planes of the transparent body. The calibration marks can be combined to form at least two groups of calibration marks, wherein at least one of the groups of calibration marks can be activated and deactivated. The calibration marks of the group of calibration marks can be arranged within a plane in the transparent body.

The optical imaging system can be a stereoscopic optical appliance, for instance a stereo microscope such as, for example, a surgical microscope or a stereo camera. However, the optical imaging system may also be an optical imaging system in which the spatial image information item is not determined by stereoscopy. By way of example, the spatial image information item can be obtained in the case of an imaging system with only one imaging beam path by virtue of a light pattern being projected on the observation object, an object image being recorded of the observation object with the projected light pattern and the spatial information item being determined from the distortion of the light pattern in the object image.

As a result of at least some of the calibration marks in the 3D calibration body being able to be activated and deactivated in the volume of the transparent body, it is possible to largely avoid shadowing, i.e., coverage of lower lying calibration marks by higher lying calibration marks as a result of a suitable activation and deactivation of the calibration marks. Particularly, if the calibration marks are combined to form groups of calibration marks, of which at least one can be activated and deactivated, it is possible to configure the groups in such a way that they are optimized in each case for a specific calibration process. Then, it is only necessary to activate the calibration marks of the respective suitable group for the respective calibration process such that a coverage of these calibration marks by calibration marks of the group not required can be avoided. Particularly, if the groups of calibration marks are respectively arranged within a plane in the transparent body, it is possible to deactivate higher lying calibration marks if lower lying calibration marks are used. Depending on the arrangement of the calibration marks in the respective planes, it may be sufficient in this case for only a part of the calibration marks to be deactivated in higher lying planes if the patterns in the respective planes are arranged in such a way that the remaining non-deactivated calibration marks in the higher plane do not cover the calibration marks in the lower lying plane.

By way of example, the transparent body can be constructed from a stack of layers in the calibration body according to an aspect of the disclosure. Then, the calibration marks are arranged in individual layers of the stack. Such a 3D calibration body can be produced in a simple manner using known layer technologies. Here, at least one of the layers of the stack can be formed by a transparent display, for instance an LCD display, a TFT display, an LED display, an OLED display, etc., wherein the selectively activatable or deactivatable calibration marks are structures that are represented on the display. This configuration of the 3D calibration body facilitates a very high flexibility in the arrangement of the calibration marks such that the calibration body can be optimally configured to the respective use purpose. By way of example, a commercially available computer can be used for controlling the representation on the display. However, it is also possible to provide a dedicated controller for the employed transparent displays.

If the employed display or the employed displays are not self-luminescent, the 3D calibration body may moreover include a background illumination arrangement. This increases the number of transparent displays that are suitable for the 3D calibration body.

In an alternative configuration of the 3D calibration body according to another aspect of the disclosure, the layers are areal light guides, wherein the light guides are each configured in such a way that evanescent fields of the light guided in the light guides occur at their interfaces. Then, the calibration marks are formed by structures at the interfaces of the light guides at which the evanescent fields are output coupled from the respective light guide in the form of propagating electromagnetic waves. Moreover, an input coupling apparatus is present for input coupling of light into the areal light guides, wherein the input coupling apparatus facilitates the input coupling of the light into individual ones of the light guides to be activated and deactivated. In this configuration, the calibration marks of a layer are activated or deactivated by virtue of the input coupling of the light into the light guide forming the layer being activated or deactivated. In order to facilitate an activation and deactivation of the input coupling of the light into individual ones of the light guides, the input coupling apparatus may have a dedicated activatable and deactivatable light source assigned to the light guide for each light guide, said light guide only input coupling light into the light guide assigned thereto in the activated state. However, the input coupling apparatus may also have a fewer number of light sources than light guides are present, the light of said light sources being able to be supplied individually to one or more individual light guides by optical switches. In particular, only a single light source may also be sufficient in this case.

Here, evanescent fields of light should be understood to mean fields in the regions of the calibration body in which light propagation does not occur. The electromagnetic fields of light decay exponentially in these regions. By way of example, evanescent fields can be produced by virtue of total-internal reflection of the light input coupled into the light guide occurring at the interfaces of the areal light guides. Then, the light merely propagates within the light guide. By contrast, the electromagnetic fields of the light decay exponentially outside of the light guide; i.e., evanescent fields are present outside of the light guide. Calibration marks can be formed by local structures at the interfaces of the light guides in such light guides, said local structures converting the evanescent fields into electromagnetic waves capable of propagation. By way of example, the conversion can be brought about by so-called frustrated total-internal reflection or by excitation of light emission by the evanescent fields. Propagating electromagnetic waves are coupled out of the light guide at the points at which a conversion takes place. Points at which the conversion takes place can be implemented, for example, by the application of substances on the surface of the light guides, by etching the light guide surface, by impressing structures onto the surface of the light guides, by boring small holes into the surface of the light guides, by structuring the surface with the aid of lasers, or by structuring the light guide surface in any other way. Here, applied substances can be organic or inorganic substances, and the substances can optionally also be fluorescent substances.

The arrangement of calibration marks in the volume of the transparent body can have a distribution of the calibration marks in the volume of the transparent body, the spatial frequency of which changes within the transparent body. By way of example, the point density, for instance, can change if the calibration marks are provided by points in the transparent body. As an alternative to calibration marks with a changing spatial frequency, it is also possible for the arrangement of the calibration marks to have a self-similar distribution of the calibration marks in the transparent body. By way of example, self-similar distributions are known as Mandelbrot sets.

Here, the distribution of the calibration marks in the transparent body can be formed by patterns of calibration marks that are arranged in the layers of the stack of layers, wherein the patterns of calibration marks each have a distribution of the calibration marks within the respective layer, the spatial frequency of which changes within the layer, or wherein the patterns of calibration marks each have a self-similar distribution of calibration marks within the respective layer.

In the case of a changing spatial frequency, the latter can be embodied, in particular, in such a way that it reduces from the center of the transparent body towards its edge. At the same time, there is the option of the extent of the respective calibration marks also changing with the spatial frequency, for example becoming larger from the center of the transparent body towards its edge.

The calibration body for the 3D calibration with different zoom levels can have an optimal embodiment if the distribution of the calibration marks in the transparent body is formed by the pattern of calibration marks, whose spatial frequency changes within the transparent body or which have a self-similar distribution.

In the method for the spatial calibration of an optical imaging system, an arrangement of calibration marks is recorded at different distances and/or from different tilt angles of the optical imaging system relative to the arrangement of calibration marks in order to obtain a spatial information item. Then, calibration is carried out on the basis of obtained spatial information items. A 3D calibration body is used within the scope of the method. Then, the arrangement of calibration marks is formed by the calibration marks of the 3D calibration body. Calibration marks of the calibration body can be activated or deactivated in a suitable manner within the scope of this method, and so it is possible to set a suitable distribution of the calibration marks, in which lower lying calibration marks are not covered by calibration marks lying thereabove. This facilitates a quick and spatially accurate calibration of the optical imaging system. Further features and advantages of the method according to an aspect of the disclosure emerge from the configurations of the employed 3D calibration body.

The optical imaging system to be calibrated can be a stereoscopic optical appliance, for instance a stereo microscope such as, for example, a surgical microscope or a stereo camera. However, the optical imaging system may also be an optical imaging system in which the spatial image information item is not determined by stereoscopy. By way of example, the spatial image information item can be obtained in the case of an imaging system with only one imaging beam path by virtue of a light pattern being projected on the observation object, an object image of the observation object with the projected light pattern being recorded and the spatial information item being determined from the distortion of the light pattern in the object image.

Moreover, according to an aspect of the disclosure, a calibration element for calibrating an optical imaging system has a pattern of calibration marks. The pattern of calibration marks has a distribution of the calibration marks, the spatial frequency of which changes within the calibration element. Alternatively, the pattern of calibration marks can have a self-similar distribution of the calibration marks.

The optical imaging system can be a stereoscopic optical appliance, for instance a stereo microscope, e.g., a surgical microscope, or a stereo camera. However, the optical imaging system may also be an optical imaging system in which the spatial image information item is not determined by stereoscopy. By way of example, the spatial image information item can be obtained in the case of an imaging system with only one imaging beam path by virtue of a light pattern being projected on the observation object, an object image of the observation object with the projected light pattern being recorded and the spatial information item being determined from the distortion of the light pattern in the object image.

A calibration of sufficient quality can be realized for both low and high zoom levels using the pattern, whose distribution of calibration marks has a changing spatial frequency, or using the pattern of calibration marks which has a self-similar distribution of calibration marks.

Typically, the effect of an optical zoom of an optical imaging system is a scaling—and hence a magnification or a reduction in the image field—around an image point located in the vicinity of the image center. In order to be able to use a sufficient number of calibration marks for the calibration post scaling, it is advantageous if the spatial frequency of the distribution of the calibration marks increases towards the center of the calibration element. Additionally or alternatively, it is possible that the extent of the respective calibration marks also changes with the spatial frequency such that smaller calibration marks are present for high zoom levels than for low zoom levels. What this can achieve is that the calibration marks used for the respective zoom level have the same size in the image on account of the scaling by the zoom factor. Since a smaller object field is considered at a higher zoom level, said object field moreover lying in the center of the object, the respective calibration marks will become larger from the center of the calibration element towards its edge in an advantageous configuration of the calibration element. Then, the small calibration marks in the center of the calibration element are used for the calibration in the case of a high zoom level, whereas the large calibration marks at the edge of the calibration element are used in the case of a low zoom level. In order to have suitable calibration marks over the entire area of the image field in the case of low zoom levels, it may be advantageous if the calibration element has a second pattern of calibration marks, in which the calibration marks have a constant spatial frequency and a constant size. Since this pattern is primarily used for low zoom levels, it typically has a low spatial frequency and calibration marks with a relatively large extent.

Within the scope of the calibration element according to an aspect of the disclosure, the distribution of the calibration marks whose spatial frequency changes within the calibration element, or which represent a self-similar distribution, may be a three-dimensional distribution of calibration marks or a two-dimensional distribution. In the former case, the calibration marks are embedded in a transparent calibration body; in the latter case, they may be applied to an areal calibration element, which need not necessarily consist of transparent material but, in principle, may also be made from a transparent material.

In the method for calibrating an optical imaging system using different zoom levels, at least one image of a pattern of calibration marks is recorded at at least one zoom level of the optical imaging system. A calibration element according to an aspect of the disclosure is used in the process. Here, the pattern of calibration marks is formed by the calibration marks of the calibration element such that the pattern has a distribution of calibration marks, whose spatial frequency changes within the calibration element, or such that the pattern of calibration marks has a self-similar distribution of the calibration marks. On account of the use of the calibration element according to an aspect of the disclosure, the method is suitable both for a calibration at low zoom levels and for a calibration at high zoom levels, and thus a calibration with a sufficient quality can be realized independent of the chosen zoom level. In particular, within the scope of the method according to an aspect of the disclosure, images of the pattern of calibration marks can also be recorded in two or more zoom levels of the optical imaging system such that the calibration can be implemented on the basis of images in a plurality of zoom levels.

Figure 1:
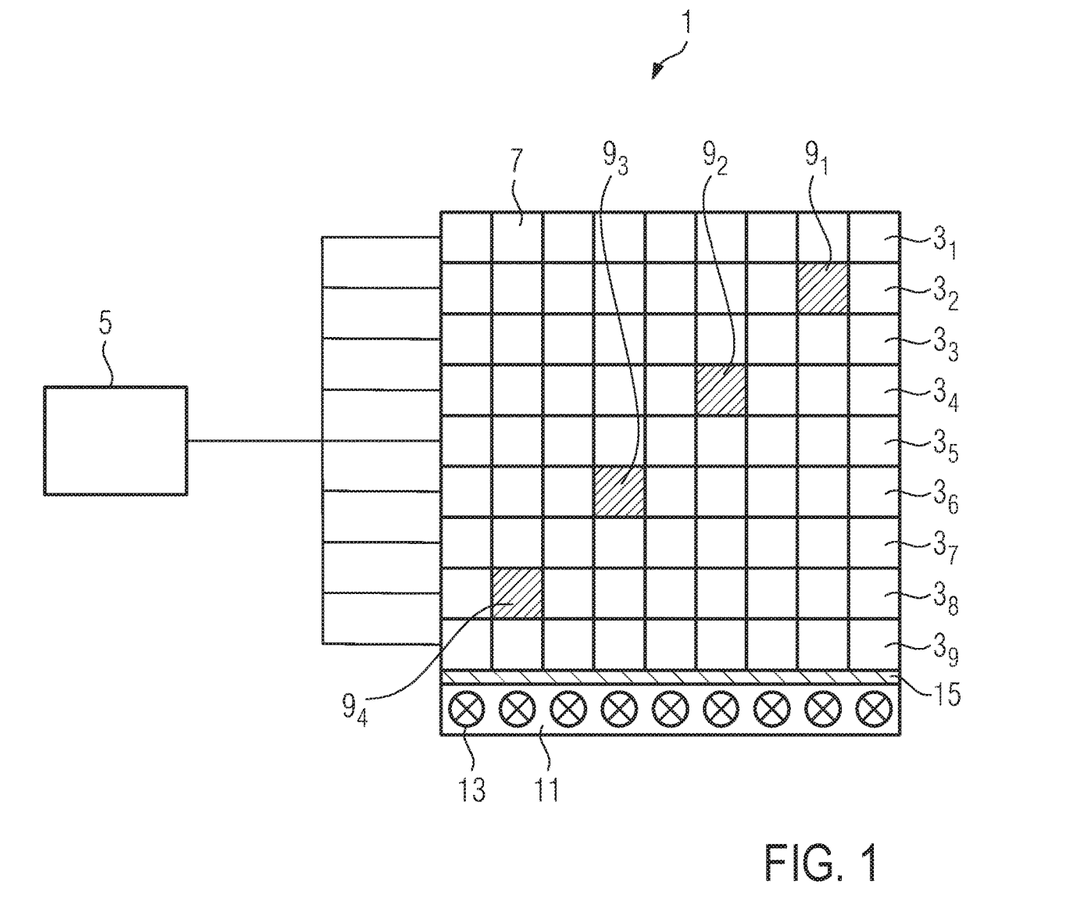

A first exemplary embodiment of a 3D calibration body is shown in FIG. 1. This calibration body is substantially formed as a stack of transparent displays $3_1$ to $3_9$, which can be actuated individually by a controller 5. Each display $3_1$ to $3_9$ includes a plurality of pixels 7, which can be individually switched into a transparent or into a non-transparent state by the controller 5. In the exemplary embodiment shown in FIG. 1, the transparent displays $3_1$ to $3_9$ form a substantially cuboid transparent body, in which most of the pixels 7 are in a transparent state. By contrast, the pixels $9_1$ to $9_4$ plotted as dark in FIG. 1 are in a non-transparent state. In the exemplary embodiment shown in FIG. 1, displays $3_1$ to $3_9$ are LCD displays, the pixels of which 7 are transparent or non-transparent, depending on the voltage applied. In the exemplary embodiment shown in FIG. 1, the stack of displays of $3_1$ to $3_9$ is illuminated by an illumination panel 11 arranged at the lower edge of the 3D calibration body 1, said illumination panel including light sources 13 which provide a background illumination of the displays $3_1$ to $3_9$. A diffuser plate 15 for equalizing the illumination intensity is located between the illumination panel 11 and the stack of displays $3_1$ to $3_9$.

Figure 2:
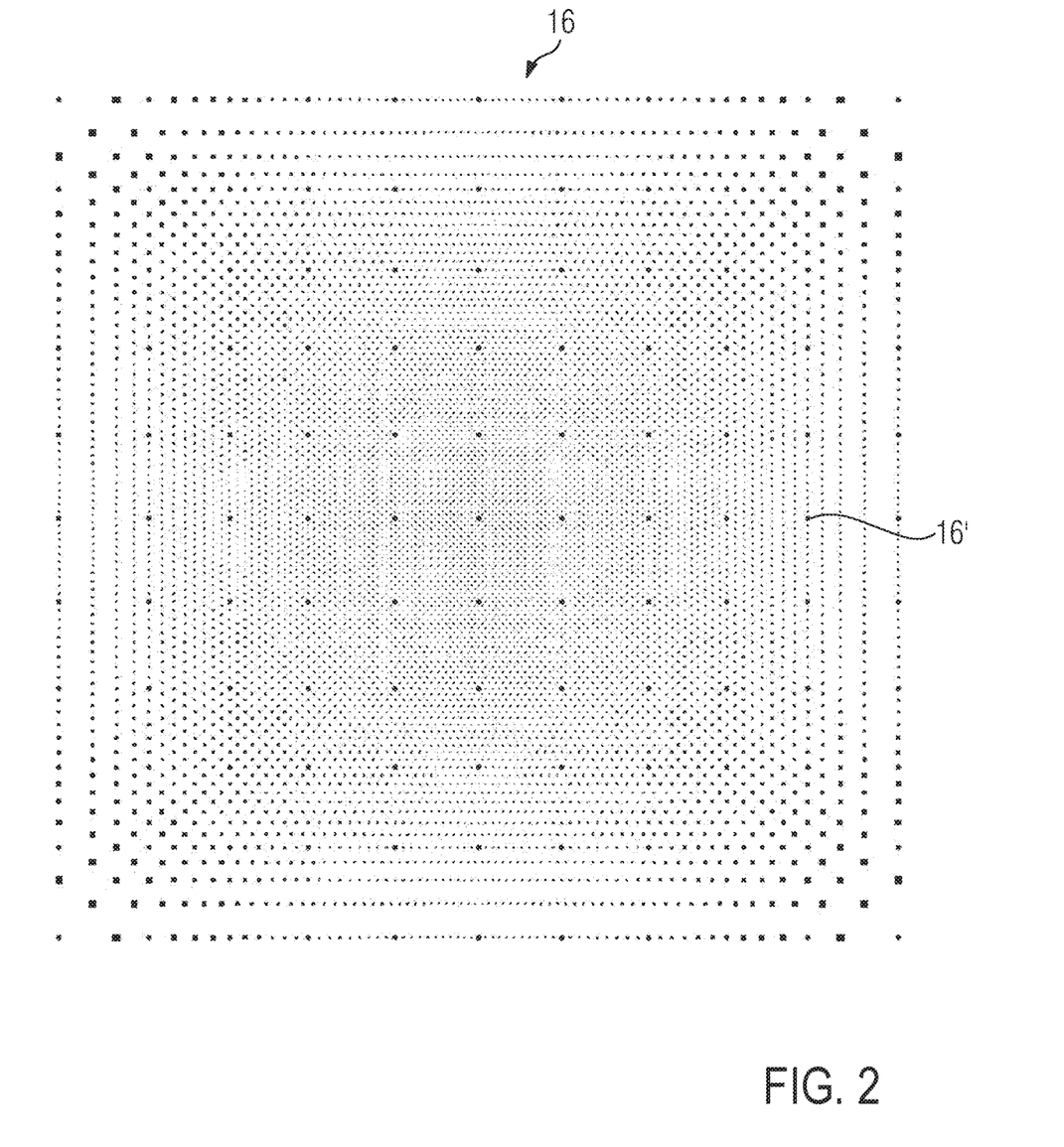

As shown in FIG. 1, the individual displays $3_1$ to $3_9$ are switched in such a way that the non-transparent pixels $9_1$ to $9_4$ lie in a plane of the substantially cuboid transparent body formed by the transparent displays $3_1$ to $3_9$, said plane running through the body in diagonal fashion. However, they may also be switched in any other way, for example in such a way that they lie in a horizontally extending plane, for example by virtue of only pixels of the display $3_5$ being switched to be non-transparent. It is likewise possible to switch pixels that lie on an imaginary curved area to be non-transparent. Moreover, unlike what is shown in FIG. 1, it is not necessary that the non-transparent pixels have constant distances from one another. Instead, pixels of the displays $3_1$ to $3_9$ can be switched to be non-transparent in such a way that the density of the non-transparent pixels is higher at the center of the 3D calibration body 1 than at the edge of the 3D calibration body 1. In this way, it is possible to create a pattern of calibration marks, said pattern having a variable spatial frequency. An example of such a pattern 16 of calibration marks is shown in FIG. 2. Furthermore, it is possible to configure calibration marks located further from the center of the 3D calibration body to be larger than calibration marks lying closer to the center of the 3D calibration body 1, as likewise shown in FIG. 2. Larger calibration marks can be obtained by virtue of calibration marks located at the edge being formed by a larger number of adjacent pixels of the displays $3_1$ to $3_9$ than small calibration marks. What can be achieved as a result of using a pattern with calibration marks of different sizes is that, in the case of different zoom levels, the calibration marks in the images recorded with the different zoom levels substantially have the same size and distances that are suitable for the calibration. Only a small section of the image is visible in the case of high zoom levels, for example the center of the 3D calibration body; by contrast, the entire calibration body 1 is visible at low zoom levels. Moreover, high zoom levels show smaller structures than low zoom levels, and therefore, the small, tightly adjacent, small calibration marks in the center of the pattern 16 can be used in a high zoom level and the less densely packed, larger calibration patterns at the edge of the pattern 16 can be used at low zoom levels. Here, it is also possible, in principle, for a pattern 16' with a constant spatial frequency, i.e., a pattern with a constant distance between the calibration marks in the entire calibration body 1, to be superposed on a pattern 16 of calibration marks with a variable spatial frequency, i.e., with distances of the calibration marks from one another, which vary over the calibration body 1. The pattern shown in FIG. 2 has such a superposition.

A pattern of calibration marks, as has been described with reference to FIG. 2, can lie within a plane formed by a display $3_1$ to $3_9$. However, reference should be made here to the fact that such a pattern need not necessarily be used in a 3D calibration body; instead, it can be used in any calibration element, in particular in an areal calibration element, too.

Figure 3:
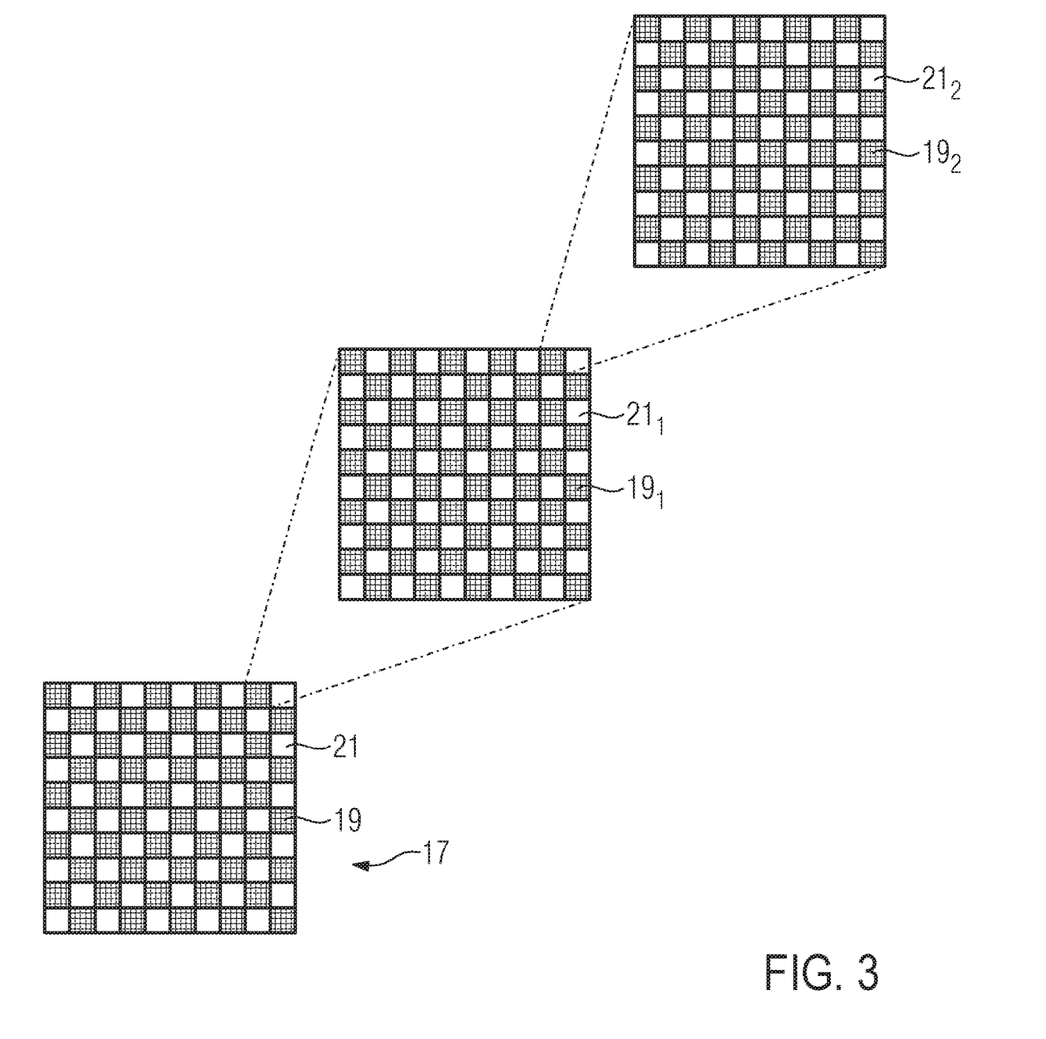

However, as an alternative to the patterns described above, it is also possible to generate self-similar patterns of calibration marks with the displays $3_1$ to $3_9$. One exemplary embodiment of such a self-similar pattern is illustrated schematically in FIG. 3. FIG. 3 shows a chequerboard-like pattern 17 made of calibration marks 19, with the calibration marks 19 in the illustrated exemplary embodiment being formed by a square area, in which a number of pixels are switched to be non-transparent. Between these calibration marks 19, there are square areas 21 of identical size, in which all pixels are switched to be transparent.

However, not all pixels in a calibration mark 19 are switched to be non-transparent; instead, the calibration mark itself represents, in turn, a chequerboard-like pattern made of now smaller square calibration marks $19_1$ with transparent square areas $21_1$ of identical size located therebetween. In the exemplary embodiment shown in FIG. 3, the smaller calibration marks $19_1$ are also formed by a display region in which a number of pixels $19_2$ are switched to be non-transparent and a number of pixels $21_2$ are switched to be transparent. In this way, each of the smaller calibration marks $19_1$, in turn, still has a chequerboard-like pattern, which is formed of even smaller calibration marks $19_2$ with transparently switched pixel regions $21_2$ located therebetween. This can be continued until a chequerboard-like pattern of individual pixels of the display, which are alternately switched to be transparent and non-transparent, is present. The pattern shown in FIG. 3 can either be a pattern formed within a single display $3_1$ to $3_9$ or a pattern formed by a plurality of displays, such as the pattern shown in FIG. 1, for example. Naturally, the number of transparent displays in this case is significantly higher than what is illustrated in FIG. 1.

Like the pattern of calibration marks shown in FIG. 2, the self-similar chequerboard-like pattern of calibration marks, described with reference to FIG. 3, can also be used in a plane calibration element instead of in a 3D calibration body.

Figure 4:
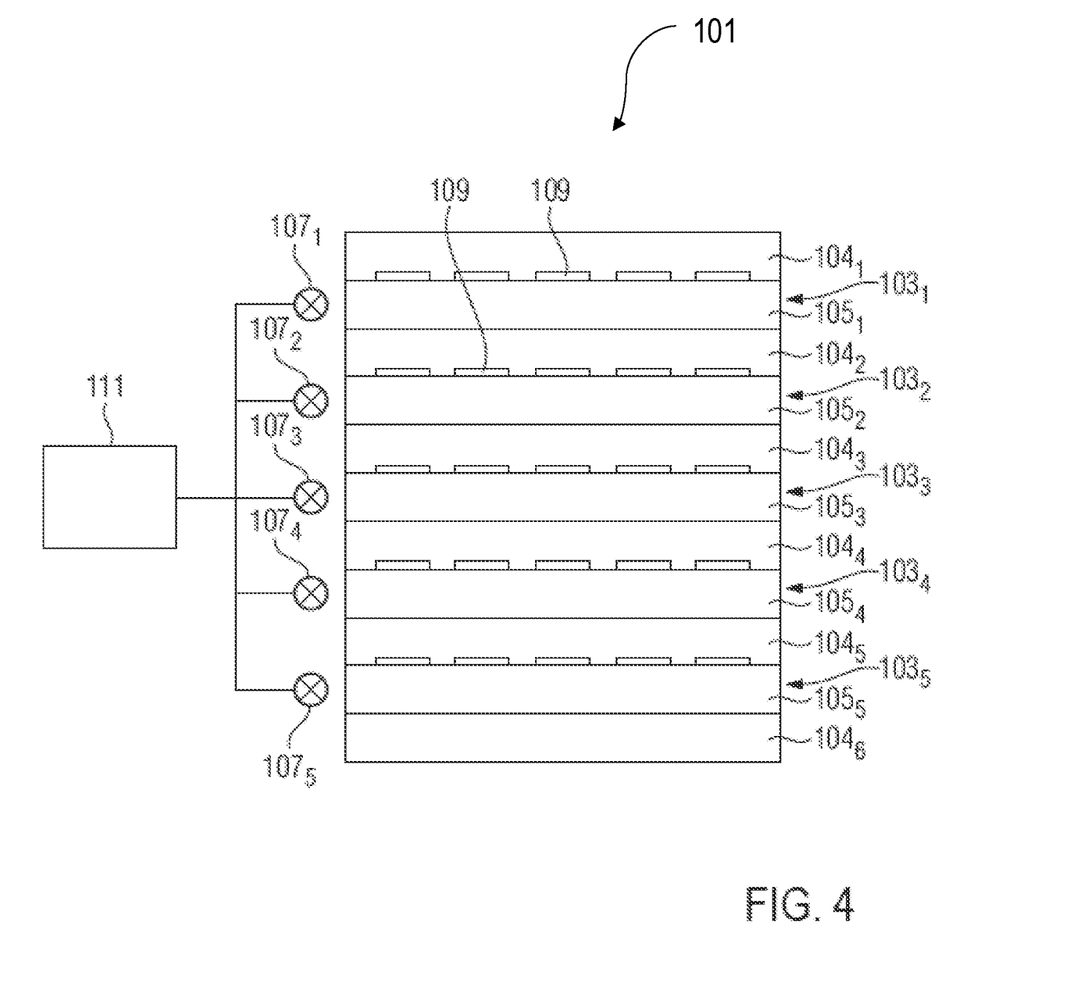

A second exemplary embodiment of a 3D calibration body is shown in FIG. 4. This calibration body 101, too, is once again substantially cuboid and made of transparent layers. In contrast to the 3D calibration body 1 of FIG. 1, the 3D calibration body 101, however, does not include a stack of transparent displays but, instead, is made of stacked light guides $103_1$ to $103_5$. The light guides $103_1$ to $103_5$ are formed by alternating transparent layers 104 and 105, with the layers $105_1$ to $105_5$ having a higher refractive index than the layers $104_1$ to $104_6$ arranged therebetween. With selectively switchable light sources $107_1$ to $107_5$, light is coupled into the layers $105_1$ to $105_5$ in such a way that it undergoes total-internal reflection at the interfaces between the layers 104 and 105. Total-internal reflection can be obtained by virtue of the high refractive index of the layers $105_1$ to $105_5$ and the low refractive index of the layers $104_1$ to $104_5$ and the incoming radiation direction of the light being matched to one another in such a way that the critical angle for total-internal reflection is exceeded.

There is light propagation, i.e., a propagation of electromagnetic waves of the light, only within the respective light guides $103_1$ to $103_5$ on account of the total-internal reflection at the interfaces between the layers 104 and 105. By contrast, the electromagnetic fields of the light decrease exponentially in the layers $104_1$ to $104_6$ with the low refractive index, and thus no propagation of the light occurs in these layers. The exponentially decaying electromagnetic fields are also referred to as evanescent fields.

In order to be able to represent calibration marks in the light guides $103_1$ to $103_5$ of the 3D calibration body 101, thin films 109 are applied at certain distances on the layers $105_1$ to $105_5$ in this exemplary embodiment. Here, the refractive index of these films is chosen in such a way that the total-internal reflection is suppressed at these points such that there is light propagation into the layers $104_1$ to $104_6$ with a low refractive index. By way of example, to this end, the refractive index of the films 109 has a value lying between the high refractive index of the layers 105 and the low refractive index of the layers 104.

If light is now coupled into one of the light guides $103_1$ to $103_5$, the light is output coupled from the light guide at those points at which the films 109 have been applied such that luminous points arise in the volume of the transparent body constructed from the layers 104, 105, said luminous points serving as calibration marks. The luminous points arise at different depths of the transparent body depending on which light sources $107_1$ to $107_5$ are activated. In order to be able to individually choose the depth at which calibration marks should be represented, the individual light sources $107_1$ to $107_5$ can be selectively activated and deactivated by a control device 111.

In the exemplary embodiment shown in FIG. 4, light is output coupled from the light guides 103 by virtue of local films 109 with a suitable refractive index being applied to the layers 105 with the low refractive index. However, it is alternatively also possible to achieve output coupling by virtue of the angle of incidence of the light on the interface between the layers 104 and 105 being modified locally in such a way that the critical angle for total-internal reflection is undershot at the corresponding points. By way of example, a local change in the angle of incidence can be produced by virtue of the orientation of the interface between the layers 104 and 105 being structured locally by lasers, by impressing, by boring, by etching or by other suitable structuring methods.

In respect of the films 109 that assist with the output coupling, it is also possible to generate the output coupling not by way of the suitable choice of a refractive index but by virtue of the evanescent fields inducing an emission of electromagnetic waves in the thin films, for example by virtue of exciting fluorescence.

Calibration marks are generated in the volume of a transparent body in the described exemplary embodiments. It is understood that, as a rule, such a body is not 100% transparent. Variations in the transparency may also be present. The volume of the calibration body should therefore always be considered to be transparent if the Michelson contrast in the body is less than 0.2, in particular less than 0.1, apart from at the points at which the calibration marks are located.

Figure 5:
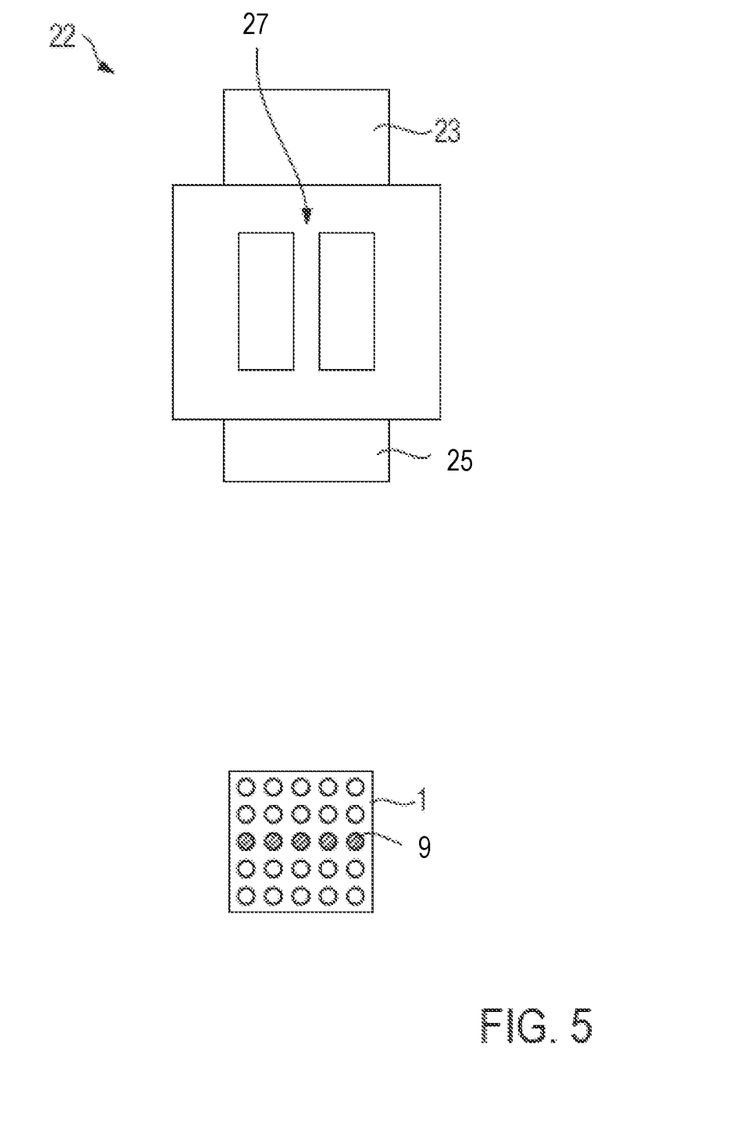

A method for the spatial calibration of an optical imaging system 22 is described below with reference to FIG. 5. The method is described on the basis of the calibration of an optical imaging system 22, which is embodied as a stereo microscope that has been equipped with a camera 23. In the exemplary embodiment shown in FIG. 5, a 3D calibration body 1, as has been described with reference to FIG. 1, is used for calibration purposes. However, it is self-evident that use can also be made of a calibration body 101, as has been described with reference to FIG. 4.

Images of the 3D calibration body 1 are successively recorded in this exemplary embodiment for the purposes of calibrating the optical imaging system, which in addition to the camera at least still include a main objective lens 25 and a zoom system 27, with different arrangements of calibration marks being present in the 3D calibration body. FIG. 5 shows how an image of calibration marks is recorded, said calibration marks being arranged approximately in the center of the calibration body in a plane that extends perpendicular to the optical axis of the imaging system. Depending on the type of calibration to be undertaken, this image may already suffice for carrying out the calibration. However, images are additionally recorded at different distances from the main objective lens 25 in other calibration processes, with calibration marks extending in different planes that are perpendicular to the optical axis of the imaging system to be calibrated. In some types of calibration, it may be additionally or alternatively be necessary for images to be recorded of calibration marks arranged in planes that are not arranged perpendicular to the optical axis of the optical imaging system to be calibrated. In this case, use can be made, for example, of a configuration of the calibration marks as illustrated in FIG. 1. It is likewise possible to use a configuration of calibration marks in which the calibration marks lie on an imagined curved surface instead of in a plane surface.

The information items necessary for the calibration can be obtained from the position of the calibration marks in the images of the calibration body 1 recorded by the optical imaging system and the calibration can finally be carried out on the basis of a suitable algorithm.

If a calibration should take place in various zoom levels of the zoom system 27, it is advantageous if the calibration body 1 is able to generate a pattern of calibration marks which has a variable spatial frequency, or which is self-similar. In particular, it is possible to use patterns of calibration points as have been described with reference to FIGS. 2 and 3.

Even though a 3D calibration is described with reference to FIG. 5, in the exemplary embodiment of a calibration of an optical imaging system, it is also possible to carry out a 2D calibration with different zoom settings. In this case, an areal calibration element can be used instead of a 3D calibration body, said areal calibration element having a pattern of calibration marks whose spatial frequency changes within the areal calibration element, as shown in FIG. 2 in an exemplary manner. Alternatively, it is possible for the employed areal calibration element to be provided with a pattern of calibration marks which have a self-similar distribution, as shown in FIG. 3 in exemplary fashion. If an areal calibration element is used, the latter naturally need not be transparent. In that case, the calibration marks could also be printed onto the areal calibration element, for example.

The present disclosure has been explained in detail on the basis of exemplary embodiments for explanatory purposes. However, a person skilled in the art will appreciate that they may depart from details of these exemplary embodiments. By way of example, transparent TFT displays could also be used instead of transparent LCD displays in the calibration body 1 of the first exemplary embodiment shown in FIG. 1. Moreover, it is possible, as a matter of principle, to use self-luminous displays, for instance LED displays or OLED displays. The illumination panel and the diffuser can then be dispensed with. At this point, reference is also made, once again, to the fact that the number of layers of the 3D calibration bodies and/or the number of pixels in the layers need not correspond to the number of layers illustrated in the figures or the number of pixels illustrated in the figures. In particular, a very high number of layers and/or a very high number of pixels may be present, for as long as this does not reduce the transparency of the volume of the 3D calibration body too much. In particular, the lower-most layers of the 3D calibration body must be sufficiently visible through the layers located thereabove.

In respect of the exemplary embodiment described with reference to FIG. 5, reference is made to the fact that the films for bringing about output coupling are illustrated significantly larger than they actually are in a real calibration body so as to aid identifiability in FIG. 5. The lower structures not being covered by upper structures is decisive for the quality of the calibration in a real calibration body. Although this may be achieved by a lateral offset of lower structures in relation to structures lying thereover in telecentric imaging systems, this, however, will not suffice in the case of non-telecentric systems. If the size of the individual structures that aid in output coupling of the light from the light guides can be kept sufficiently small, a coverage in the case of calibration marks, which are arranged with an offset, in the different planes of the light guides can be obtained with the smallest possible coverage of lower-lying calibration marks by calibration marks lying thereabove. Since, as a matter of principle, infinitesimal films or infinitesimal regions with an angle of incidence that is suitable for output coupling at the interfaces between the layers with a high and a low refractive index suffice for output coupling the light from the light guide, the films or the introduced structures can be kept very small. This allows coverage to be largely avoided such that also a plurality of planes of calibration marks can be used at the same time.

With reference to the self-similar distribution of calibration marks in FIG. 3, reference is made to the fact that the pattern may also be constructed from geometric forms other than quadratic areas, for instance from other polygonal areas such as triangular areas or hexagonal areas. Irregular structures, too, are conceivable as a matter of principle.

Since it is possible to deviate from the individual described exemplary embodiments in a manner evident to a person skilled in the art, the present disclosure should not be restricted by the described exemplary embodiments.

LIST OF REFERENCE NUMERALS

1 Calibration body
3 Transparent display
5 Controller
7 Transparent pixel
9 Non-transparent pixel
11 Illumination panel
13 Light source
15 Diffuser
16 Pattern
17 Pattern
19 Calibration mark
21 Transparent region
22 Optical imaging system
23 Camera
25 Main objective lens
27 Zoom system
101 Calibration body
103 Light guide
104 Layer with a high refractive index
105 Layer with a low refractive index
107 Light source
109 Film
111 Control device

What is claimed is:

1. A 3-dimensional (3D) calibration body for a spatial calibration of an optical imaging system, the 3D calibration body comprising:
   a transparent body having a volume; and
   calibration marks embedded in the volume of the transparent body, at least some of the calibration marks being selectively activatable and deactivatable by a controller, and
   an activated calibration mark being visible in a visible spectral range and a deactivated calibration mark not being visible in the visible spectral range,
   wherein the transparent body is made of a stack of layers,
   wherein the calibration marks are arranged in individual layers of the stack of layers,
   wherein the individual layers form areal light guides with interfaces,
   wherein each of the areal light guides is configured such that evanescent fields of light guided in the light guides occur at the interfaces of the light guides,
   wherein the calibration marks are formed by structures at the interfaces of the light guides at which the evanescent fields are output coupled from the respective light guides as propagating electromagnetic waves,
   wherein an input coupling apparatus input couples the light into the areal light guides, and
   wherein the input coupling apparatus renders it possible to activate and deactivate input coupling of the light into individual ones of the areal light guides.

2. The 3D calibration body according to claim 1, wherein the calibration marks are selectively activatable and deactivatable in different planes of the transparent body.

3. The 3D calibration body according to claim 1, wherein the calibration marks are combined to form at least two groups of calibration marks and at least one of the groups of calibration marks is activatable and deactivatable.

4. The 3D calibration body according to claim 3, wherein the calibration marks of a group of the at least two groups of calibration marks are arranged within a plane in the transparent body.

5. The 3D calibration body according to claim 1, wherein:
   at least one of the individual layers of the stack of layers is formed by a transparent display, and
   the selectively activatable and deactivatable calibration marks are structures displayed on the transparent display.

6. The 3D calibration body according to claim 5, further comprising:
a background illumination arrangement for the at least one of the individual layers formed by the transparent display.

7. The 3D calibration body according to claim 1, wherein:
total-internal reflection of the light input coupled into the areal light guides occurs at the interfaces of the areal light guides, and
the calibration marks are formed by local structures at the interfaces of the areal light guides, at which a conversion takes place from the evanescent fields into electromagnetic waves capable of propagation.

8. The 3D calibration body according to claim 1, further comprising an arrangement of the calibration marks, wherein:
the arrangement of the calibration marks has a distribution of the calibration marks in the transparent body, a spatial frequency of which changes within the transparent body, or
the arrangement of calibration marks has a self-similar distribution of the calibration marks in the transparent body.

9. The 3D calibration body according to claim 8, wherein:
the distribution of the calibration marks in the transparent body is formed by patterns of the calibration marks arranged in the layers of a stack of layers, each of the patterns of the calibration marks has a distribution of the calibration marks within a respective layer, the spatial frequency of which changes within the layer, or
the patterns have a self-similar distribution of the calibration marks.

10. The 3D calibration body according to claim 8, wherein the spatial frequency is reduced from a center of the transparent body towards an edge of the transparent body.

11. The 3D calibration body according to claim 8, wherein an extent of respective calibration marks changes with the spatial frequency.

12. The 3D calibration body according to claim 11, wherein the extent of the respective calibration marks increases from a center of the transparent body towards an edge of the transparent body.

13. A method for spatial calibration of an optical imaging system, the method comprising:
recording an arrangement of calibration marks at different distances and/or different tilt angles of the optical imaging system relative to an arrangement of the calibration marks to obtain a spatial information item,
carrying out the spatial calibration based on the spatial information item obtained with the 3D calibration body according to claim 1, and
forming the arrangement of the calibration marks with the calibration marks of the 3D calibration body.

\* \* \* \* \*